(12) United States Patent
Kemppainen et al.

(10) Patent No.: US 8,020,790 B2
(45) Date of Patent: Sep. 20, 2011

(54) BIOLOGICAL SAMPLE DISRUPTION TECHNIQUES

(75) Inventors: Jon Kemppainen, Austin, TX (US); Gary J. Latham, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 697 days.

(21) Appl. No.: 10/576,661

(22) PCT Filed: Oct. 21, 2004

(86) PCT No.: PCT/US2004/034850
§ 371 (c)(1),
(2), (4) Date: May 2, 2008

(87) PCT Pub. No.: WO2005/039722
PCT Pub. Date: May 6, 2005

(65) Prior Publication Data
US 2008/0223962 A1    Sep. 18, 2008

Related U.S. Application Data

(60) Provisional application No. 60/514,313, filed on Oct. 24, 2003.

(51) Int. Cl.
*B02C 17/18* (2006.01)
(52) U.S. Cl. .......................... 241/2; 241/184
(58) Field of Classification Search ............... 241/2, 21, 241/30, 184
See application file for complete search history.

(56) References Cited

U.S. PATENT DOCUMENTS

| | | | | |
|---|---|---|---|---|
| 983,028 | A | * | 1/1911 | Davidsen ............. 241/184 |
| 1,864,542 | A | * | 6/1932 | Holzapfel ............ 241/184 |
| 2,069,731 | A | | 2/1937 | Trumpler ................ 264/5 |
| 2,847,169 | A | * | 8/1958 | Hartman ............. 241/184 |
| 4,634,062 | A | | 1/1987 | Berchem ............. 241/184 |
| 4,775,393 | A | * | 10/1988 | Boecker et al. ......... 51/293 |
| 5,390,859 | A | * | 2/1995 | Rajasekaran ............. 241/2 |
| 5,829,696 | A | * | 11/1998 | DeStefano et al. .... 241/169 |
| 5,921,477 | A | | 7/1999 | Tomes et al. ............. 241/2 |
| 6,258,930 | B1 | | 7/2001 | Gauch et al. ........... 530/300 |
| 6,579,002 | B1 | | 6/2003 | Bartick et al. .......... 366/112 |
| 6,755,364 | B2 | * | 6/2004 | Lugmair et al. ......... 241/24.1 |

FOREIGN PATENT DOCUMENTS
WO    WO 2005/039722    5/2005

OTHER PUBLICATIONS

"Beads," www.biospec.com/Beads.htm, BioSpec Products, Inc. visited Oct. 23, 2003.
International Search Report from PCT Application No. PCT/US04/34850 mailed Jun. 1, 2005.
Written Opinion from PCT Application No. PCT/US04/34850 mailed Jun. 1, 2005.
International Preliminary Report on Patentability from PCT Application No. PCT/US04/34850 mailed Apr. 24, 2006.

* cited by examiner

*Primary Examiner* — Mark Rosenbaum

(57) ABSTRACT

Improved ball mill disruption techniques. In different embodiments, disrupting particles that are not substantially spherical are used. In other embodiments, roughened disrupting particles are used. In other embodiments, larger disrupting particles are used. In each instance, improved disruption can be achieved.

6 Claims, 10 Drawing Sheets

BALLCONE

Designed to combine the action of balls and cones with one scientifically proportioned shape.

| Order by Size | Dimensions A | B |
|---|---|---|
| 1/8" | .125 | .170 |
| 5/32" | .215 | .270 |
| 3/16" | .270 | .300 |
| 1/4" | .320 | .400 |
| 5/16" | .375 | .465 |

FIG. 13A

DIAGONALS

Beveled edges of diagonally-cut ends provide effective finishing action in corners. Cylindrical body offers wide area contacts.

| Order by Size | Dimensions A | B | B |
|---|---|---|---|
| 1/8" | .125 | .125 | .225 |
| 5/32" | .156 | .156 | .275 |
| 3/16" | .187 | .187 | .325 |
| 7/32" | .218 | .218 | .380 |
| 1/4" | .250 | .250 | .445 |
| 5/16" | .312 | .312 | .545 |
| 3/8" | .375 | .375 | .655 |

FIG. 13B

PINS Tapering to pointed ends, pins reach into the recesses of figured work and grooves, deflash through-holes and clean threaded areas.

| SLIM (S) | TAPER (T) |
|---|---|
| 3/64" x 3/8" | 3/32" x 3/8" |
| 3/64" x 1/2" | 1/8" x 3/8" |
| 1/16" x 9/32" | 1/8" x 1/2" |
| 1/16" x 1/2" | 5/32" x 1/2" |

FIG. 13C

BIOLOGICAL SAMPLE DISRUPTION TECHNIQUES

This application is a national phase application under 35 U.S.C. §371 of International Application No. PCT/US2004/034850 filed 21 Oct. 2004, which claims the benefit of U.S. Provisional Application No. 60/514,313 filed 24 Oct. 2003, the contents of which are incorporated herein by reference in their entirety.

This application claims priority to U.S. Provisional Patent Application Ser. No. 60/514,313 filed Oct. 24, 2003, which is hereby incorporated by reference.

STATEMENT AS TO RIGHTS TO INVENTION MADE UNDER FEDERALLY-SPONSORED RESEARCH AND DEVELOPMENT

Aspects of this invention were made with government support of the National Cancer Institute of the National Institutes of Health Department, grant number 1 R43 CA97482-01. The government may have certain rights in this invention.

BACKGROUND OF THE INVENTION

1. Field of the Invention

Embodiments of the present invention relate generally to sample disrupters such as ball mills (also called bead mills). More particularly, representative embodiments concern the use of irregular disrupting particles, instead of standard balls, that more effectively disrupt samples.

2. Description of Related Art

For a number of applications, the need has arisen for hands-off disruption of samples such as biological samples. In particular, there is a need to disrupt gram-sized biological samples. This need is particularly acute for molecular diagnostics using clinical specimens. Historically, samples in this size range have been processed by mortar and pestle followed by homogenization using a rotor-stator device (polytron) followed by purification by organic extraction or on a glass filter.

Several vendors currently sell closed-tube tissue disrupter systems in which disruption of a sample is achieved by agitating the sample in a lysis buffer in the presence of a disrupting media. This media is typically 1-2.5 mm spherical balls or beads made of stainless steel, zirconium, or other dense material. Advantages for this "closed system" approach include: (a) no release of irritating or toxi aerosols; (b) fast processing (~2 to 4 minutes); (c) less potential for sample to sample cross-contamination; (d) ease of operation; (f) relatively maintenance free; (g) easy use in a clinical setting; and (h) potentially disposable.

Example commercial products include the MIXER MILL MM 300 by QIAGEN, the FASTPREP instrument by QBIOGENE, and the MINIBEADBEATER by BioSpec.

Although these commercial products work well and can produce, e.g., high-quality RNA from biological samples, drawbacks nevertheless exist. First, commercial machines capable of homogenizing large samples can be relatively expensive. Second, the total amount of biological sample that can be efficiently disrupted using these machines is limited (e.g., it is believed that the amount is currently about 30 mg for the commercial MM 300 device to about 300 mg for the commercial FASTPREP device). Third, commercially-available disrupters often take too long to disrupt samples and particularly relatively large samples. Depending on the type of sample being disrupted, this may not be a major concern. However, if the sample being disrupted is a biological sample, it is beneficial to achieve the most efficient, rapid disruption possible. To isolate biological materials, a cell structure typically has to be destroyed. This lysis should be accomplished very rapidly, if possible, in the most efficient manner possible because nucleic acids (particularly RNA) can degrade rapidly after the destruction of a cell structure.

The referenced shortcomings of conventional methodologies mentioned above are not intended to be exhaustive, but rather are among many that tend to impair the effectiveness of previously known techniques concerning disrupters. Other noteworthy problems may also exist; however, those mentioned here are sufficient to demonstrate that methodology appearing in the art has not been altogether satisfactory and that a significant need exists for the techniques described and claimed here.

SUMMARY OF THE INVENTION

Shortcomings of the conventional systems are reduced or eliminated by the techniques disclosed here. These techniques are applicable to a vast number of applications, including but not limited to any application involving disruption of a sample using a disrupting media.

Procedures described here are able to more effectively disrupt samples including biological samples. Disruption occurs more quickly and on larger sample sizes. In addition to the greater efficiency, the present techniques do not suffer from reduced extraction yields of useful nucleic acids such as RNA. In fact, the inventors have found that using the techniques of this disclosure can actually increase nucleic acid yield from a disrupted sample. In other words, the present techniques can allow a user to more quickly disrupt larger samples, yet retrieve more RNA and other nucleic acids than would be retrieved using conventional techniques.

An embodiment of the invention involves a method including disrupting a biological sample in a ball mill loaded with disrupting particles that are not substantially spherical. The particles can have a jagged surface. The particles can have one or more sharp edges or corners. The particles can include screw-bits, cone balls, pins, or non-spherical shot.

An embodiment of the invention involves a method including disrupting a biological sample in a ball mill loaded with substantially spherical disrupting particles that have been roughened prior to use. The particles can be roughened by sanding, forming grooves within a surface of the particles, a ball peening process, an electric discharge processes, or by embedding a material within a surface of the particles.

An embodiment of the invention involves a method including increasing a yield of nucleic acids from a biological sample by disrupting the sample in a ball mill loaded with disrupting particles that are not substantially spherical instead of substantially-spherical disrupting particles of about the same size and density. Increasing the yield may also accompany an improved 28S/18S ratio.

An embodiment of the invention involves a method including decreasing the disruption time of a biological sample by disrupting the sample in a ball mill loaded with disrupting particles that are not substantially spherical instead of substantially-spherical disrupting particles of about the same size and density.

An embodiment of the invention involves a method including disrupting a biological sample in a ball mill that includes a vial having an inner surface that is jagged or has been roughened prior to use. The inner surface can be roughened by sanding, forming grooves within the surface, a ball peening process, an electric discharge processes, or by embedding a material within the surface.

An embodiment of the invention involves a method including disrupting a biological sample in a mill that includes a vial with an internal grill configured to contribute to disruption. The mill can be a ball mill.

An embodiment of the invention involves an apparatus including a ball mill including disrupting particles (a) that are not substantially spherical or (b) that are substantially spherical, which have been roughened prior to use.

An embodiment of the invention involves an apparatus including a ball mill including a vial having an inner surface that has been roughened prior to use.

An embodiment of the invention involves an apparatus including a ball mill including a vial with an internal grill configured to contribute to disruption.

An embodiment of the invention involves a kit including: (1) disrupting particles (a) that are not substantially spherical or (b) that are substantially spherical, which have been roughened prior to use; and (2) a lysis buffer for biological samples.

An embodiment of the invention involves a method including disrupting a biological sample in a ball mill using disrupting particles having a largest dimension greater than or about equal to 4 mm, the method not comprising plating of yeast or bacteria. The particles can be of any shape, whether substantially spherical or not substantially spherical. The particles can include steel spheres. The spheres can have a diameter of $3/16$, or $7/32$ inches. The particles can include diagonals and/or coneballs, in some preferred embodiments.

Unless explicitly noted otherwise, throughout this disclosure and its history within the Patent Office, the term "biological sample" denotes all materials that are produced by biological organisms or can be isolated from them; in particular, they denote materials that contain nucleic acids and/or proteins. The term "biological sample" includes untreated or pretreated samples, e.g. plasma, body fluids, particularly blood, sputum, urine, feces, sperm, cells or cell cultures, serum, leukocyte fractions, smears, tissue samples of all kinds, plants and parts of plants, microorganisms such as bacteria, viruses such as cytomegalo virus, HIV, hepatitis B, hepatitis C, hepatitis δ virus, yeasts, embryos, fungi, cell-free sample material, etc. The term also includes both a mixture of the above-mentioned samples such as fungus-infected plants or whole human blood containing mycobacteria as well as food samples that contain free or bound nucleic acids or cells containing nucleic acids, environmental samples which contain free or bound nucleic acids or cells containing nucleic acids. Pretreated biological samples may be, for example, heat treated (frozen, dried, etc.) or chemically treated (e.g., fixed in suitable chemicals such as formalin, alcohol, etc.).

Unless explicitly noted otherwise, throughout this disclosure and its history within the Patent Office, the term "nucleic acids" includes all possible kinds of nucleic acids such as deoxyribonucleic acid (DNA), ribonucleic acid of all lengths and configurations, such as double-stranded, single-stranded, circular and linear, branched, etc., plasmids, viral and bacterial DNA and RNA as well as genomic or other non-genomic DNA and RNA from animal and plant cells or other eukaryotes, t-RNA, mRNA in processed and unprocessed form, hn-RNA, rRNA and cDNA and all other nucleic acids. In addition, the term includes a sample that contains nucleic acid or a sample or mixture of samples that contains nucleic acid, which may be used as suitable educts for downstream applications such as in vitro transcription, PCR reactions or cDNA syntheses.

Unless explicitly noted otherwise, throughout this disclosure and its history within the Patent Office, the term "disrupting particles" denotes any particle to be added to a sample to facilitate the disruption of that sample during agitation. For example, the term "disrupting particles" encompasses terms such as "grinding media" or "beads" that are sometimes used in the art. Sizes and shapes for disrupting particles can vary widely. Representative shapes are disclosed here and other shapes will be apparent to those of ordinary skill in the art having the benefit of this disclosure. Representative sizes are also disclosed and, in general, can typically range from about 0.5 mm to about 2.5 mm for biological applications involving milligram-sized quantities of samples. Of course, for different applications, the size may need to be different, as those of ordinary skill in the art understand.

Unless explicitly noted otherwise, throughout this disclosure and its history within the Patent Office, the term "substantially" carries its ordinary meaning (e.g., largely but not wholly that which is specified, Webster's Ninth New Collegiate Dictionary (9th ed. 1983)). Use of this term accommodates minor variations and describes embodiments of the invention with precision appropriate to this technology. Conventional beads used in the art are described as "substantially" spherical because those beads are not necessarily mathematically-perfect spheres, but may include minor imperfections that affect their shape.

Unless explicitly noted otherwise, throughout this disclosure and its history within the Patent Office, the term "ball mill" carries its ordinary meaning (e.g., a device that disrupts a sample using grinding media, typically a device utilizing vial(s) and grinding beads).

Other features and associated advantages will become apparent with reference to the following detailed description of specific, non-limiting embodiments in connection with the accompanying drawings.

BRIEF DESCRIPTION OF THE DRAWINGS

The following drawings form part of the present disclosure and are included to further demonstrate non-limiting embodiments of the present invention. Embodiments may be better understood by reference to one or more of these drawings in combination with the text of this disclosure.

FIGS. 13A-C illustrate different representative, but not limiting, media and dimensions that may be used with embodiments of the invention. Illustrated are pins, diagonals, and cone balls.

DESCRIPTION OF EXEMPLARY, NON-LIMITING EMBODIMENTS

Figure 1:
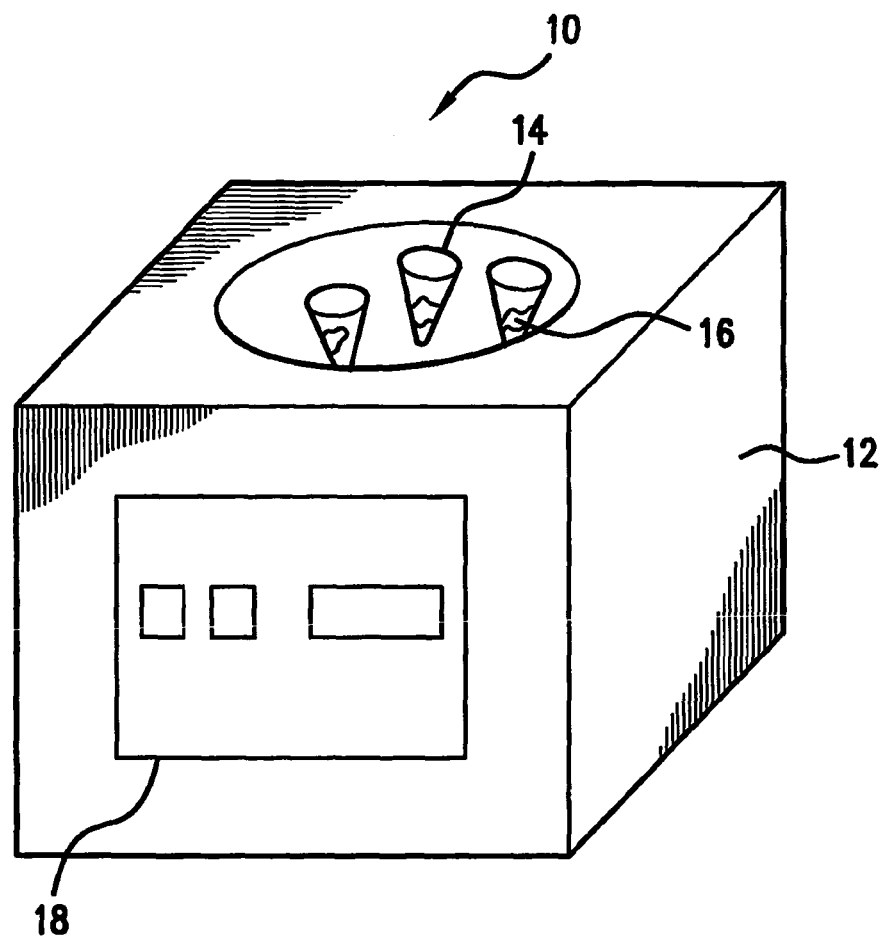
FIG. 1 is a schematic diagram of a representative ball disruption system in accordance with embodiments of the invention.

Techniques of this disclosure can readily be applied to a vast number of applications in which a sample needs to be efficiently disrupted. Techniques of this disclosure are particularly useful in applications involving the efficient lysing of hundreds of milligrams to gram quantities of tissue, although the claims or the disclosure are not limited as such.

Each figure will be discussed in turn. It will be recognized that the figures can be thought-of in terms of associated apparatuses, systems, kits, or methods. For example, when describing a figure of a vial, it will be understood that the vial can be used in an associated method (e.g., to hold material during disruption method steps), an associated apparatus or system (e.g., as part of a ball mill apparatus or system), or an associated kit (e.g., along with a buffer or other equipment). For conciseness, a separate description of each possible application will not be given, unless it would be necessary for understanding.

The ball mill 12 can be any of the commercially available ball mills on the market including, but not limited to, those mentioned in the "Description of Related Art" section above. For example, the MINIBEADBEATER (BioSpec) may be utilized. Control panel 18 is meant to provide any type of generic control over the bead mill. In different embodiments, it may control parameters such as speed, duration of disruption, etc. The capabilities (e.g., sample capacity, motor speed, vibration controls, etc.) of ball mills 12 can vary widely, as is known the in the art. What ball mill 12 represents is any ball mill sufficient to disrupt samples such as, but not limited to, gram sized biological samples.

Vials 14 are intended to contain one or more samples along with disrupting particles and couple (i.e., direct or indirect connection or association) to the ball mill 12 to achieve disruption. In representative embodiments, vials 14 can include any commercially available vials known in the art. In other embodiments discussed below, vials 14 can include a roughened inner surface and/or an internal grill that facilitates the disruption process. Sizes and materials of the vials 14 can vary widely, as is known the in the art. What vials 14 represent are any vials sufficient to hold samples and disrupting particles for ball mill 12. In other embodiments (not drawn), vials 14 can of course be integral with ball mill 12. In other words, a separate container may not be needed to hold samples and disrupting particles. Instead, such material can be part of the ball mill 12 itself.

The design and concept behind disrupting particles 16 are significant to this disclosure, for they can provide for significantly improved disruption. Generally, disruptive particles 16 are designed to be different than typical grinding media used today. That grinding media consists of substantially spherical balls or beads.

Figure 2:
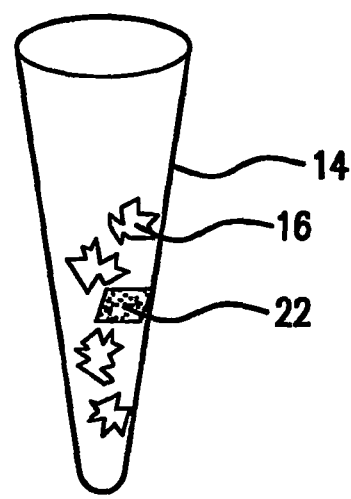
FIG. 2 is a schematic diagram of a representative vial with a sample and disrupting particles in accordance with embodiments of the invention.
Figure 3:
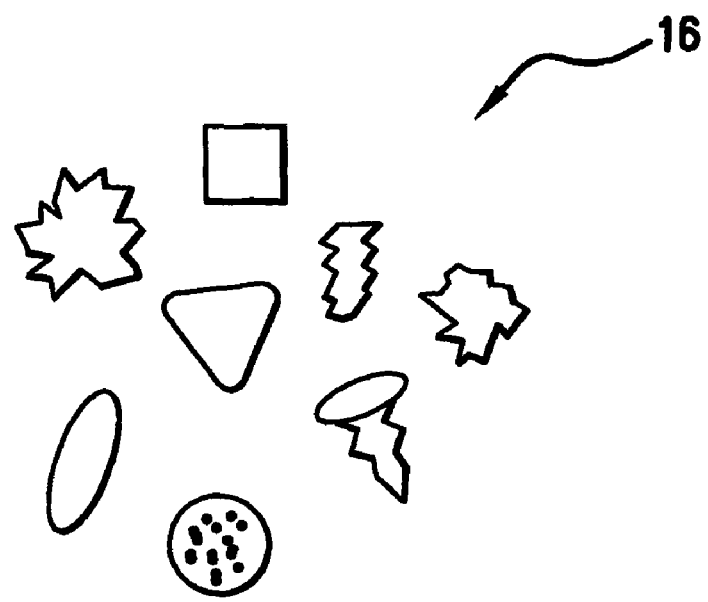
FIG. 3 is a schematic diagram of representative disrupting particles in accordance with embodiments of the invention.

FIG. 2 is a schematic diagram of vial 14 with a sample 22 and disrupting particles 16. As shown, disrupting particles 16 are not substantially spherical. Instead, they can have a jagged surface and/or one or more sharp edges or corners. Additionally, they can be substantially spherical but roughened prior to use (discussed in more detail below). FIG. 3 is a schematic diagram of representative disrupting particles 16. Disrupting particles 16 can be loaded into a vial 14 such that a heterogeneous population of small and large particles exist. In fact, the inventors have found that such a mixing can be particularly beneficial in effecting improved disruption.

Figures 4A, 4B, 4C:
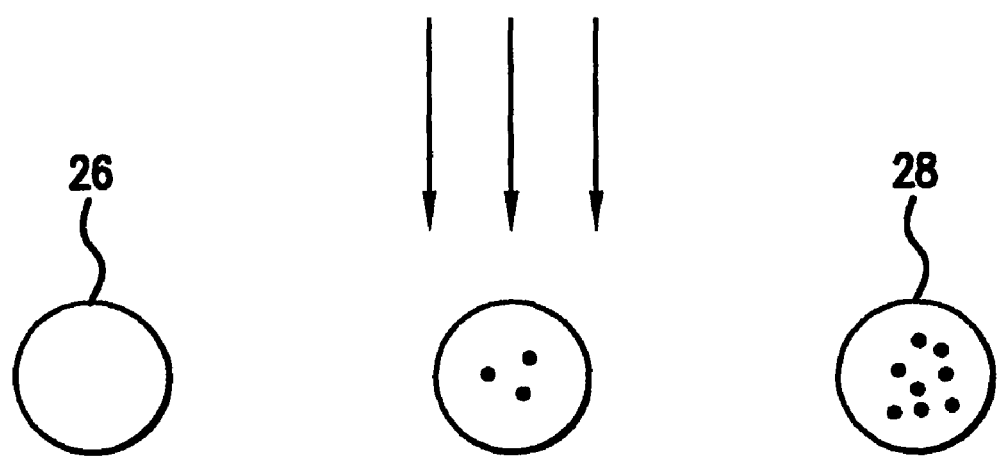
FIGS. 4A-C are schematic diagrams showing how disrupting particles can be roughened, in accordance with embodiments of the invention.

FIG. 4 is a schematic diagram showing how disrupting particles 16 can be roughened. In one embodiment, substantially spherical disrupting particles 26 (i.e. conventional grinding media) can be roughened prior to use to increase their effectiveness in disrupting a sample. FIG. 4 shows three general steps: in step (a) a substantially spherical disrupting particle 26 is obtained; in step (b) particle 26 is treated or processed to roughen it; in step (c) the roughening process is complete, and a roughened disrupting particle 28 is obtained. Of course, such a roughening process can be applied to disrupting particles 16 that are not substantially spherical as well.

Treatments or processing steps that can be used to achieve a roughened disrupting particles are known in related fields and can be applied here. For example, one can use any process that transforms a relatively smooth surface into a roughened surface having an increased coefficient of friction. Suitable, non-limiting methods include: sanding, forming grooves within a surface, ball peening processes, electric discharge processes, and embedding of hard particles within a surface.

An electrical discharge process can be based on the principle of removal of portions of a metal surface by spark discharges. Typically a spark is generated between the surface to be treated and an electrode by creating potential differential between the object and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. Electric discharge machines are well known. A method for forming a frictional surface within a metal surface using an electric discharge process is described in U.S. Pat. No. 4,964,641, which is incorporated by reference as if set forth herein.

A shot peening process for forming a textured surface is described in U.S. Pat. No. 5,526,664, which is incorporated by reference. In general, a shot peening process involves propelling a stream of hardened balls, typically made of steel, at a relatively high velocity at a surface. To create a pattern upon an area of the surface the stream is typically moved about the surface. The speed by which the stream is moved about the surface tends to determine the type of textured surface formed.

A textured surface can be produced by embedding sharp hardened particles in the surface. A method for embedding sharp hardened particles in a metal surface is described in U.S. Pat. No. 4,768,787, which is incorporated by reference. A laser or other high energy source can be used to heat the surface such that the surface melts in selected areas. Just before the molten area re-solidifies, a stream of abrasive particles can be directed to the area. In this manner, some of the particles tend to become embedded within the molten surface. The particles typically have a number of sharp edges that protrude from the surface after the particles have been embedded within the surface.

Figure 5:
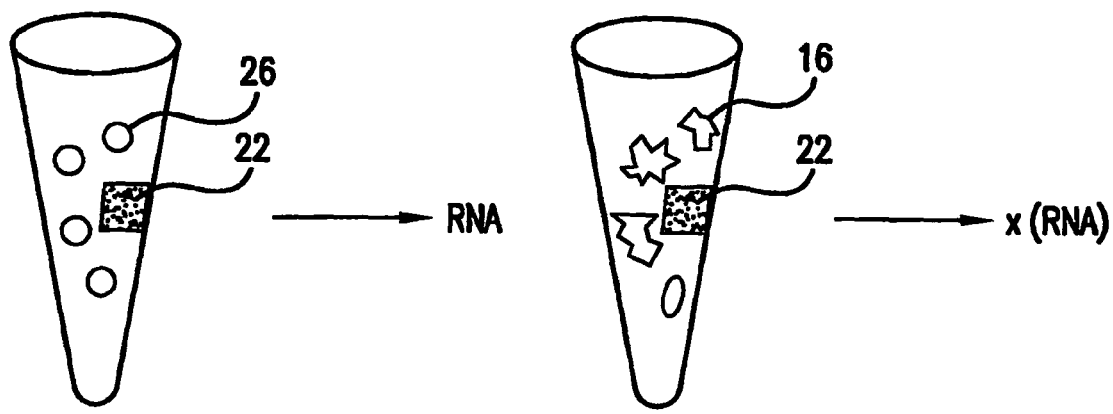
FIG. 5 is a schematic diagram showing the increasing of yield of nucleic acids, in accordance with embodiments of the invention.

FIG. 5 is a schematic diagram showing the increasing of yield of nucleic acids. FIG. 5 generally shows that a particular yield of nucleic acids can be obtained using conventional, substantially-spherical grinding media. However, when using disrupting particles 16 of the current disclosure, one can obtain an increased yield, represented in the figure by a scaling factor x that is greater than one. It will be understood by those having ordinary skill in the art that the yield comparison shown in FIG. 5 is most sound if the comparison is made with conventional disrupting particles of about the same overall size and density of the irregular disrupting particles of this disclosure.

Figure 6:
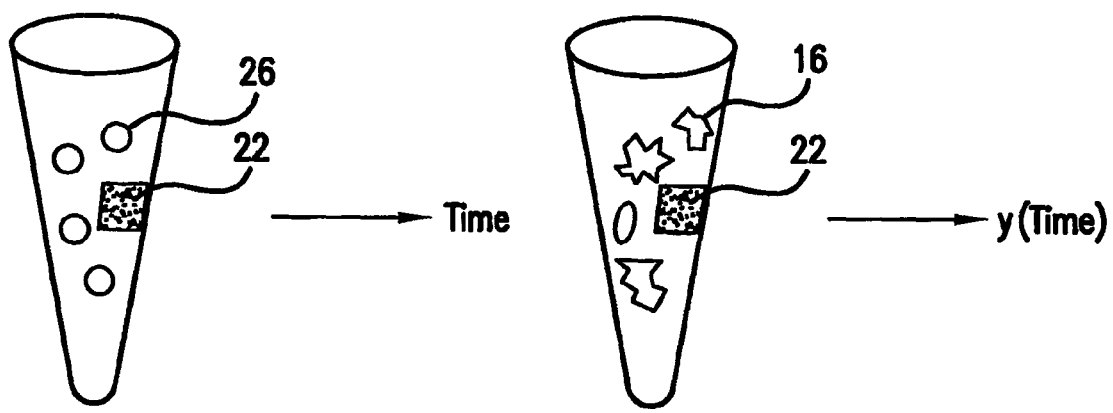
FIG. 6 is a schematic diagram showing the decreasing of disruption time, in accordance with embodiments of the invention.

FIG. 6 is similar to FIG. 5 except that FIG. 6 is directed to disruption time instead of yield. FIG. 6 conveys that one can decrease disruption time. Using conventional, substantially-spherical grinding media, one can disrupt a sample in a particular amount of time. However, when using disrupting particles 16 of the current disclosure, one can disrupt that sample in less time, represented in the figure by a scaling factor y that is less than one. As was the case with FIG. 5, it will be understood by those having ordinary skill in the art that the disruption time comparison shown in FIG. 6 is most sound if the comparison is made with conventional disrupting particles of about the same overall size and density of the irregular disrupting particles of this disclosure.

Figure 7:
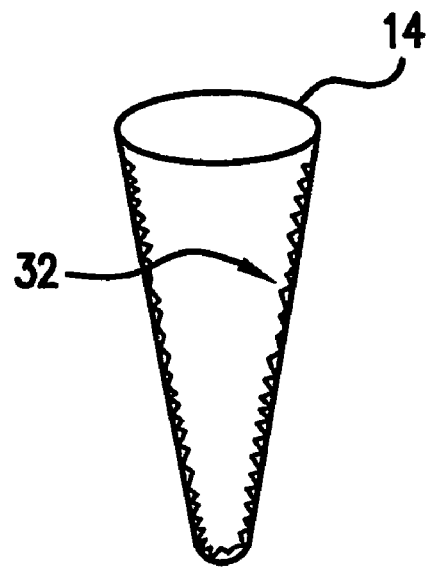
FIG. 7 is a schematic diagram of a vial having a roughened inner surface in accordance with embodiments of the invention.

FIG. 7 shows a vial 14 having a roughened inner surface 32. The inner surface 32 can be jagged. Inner surface 32 can be roughened using the procedures described above in relation to FIG. 4. Alternatively, inner surface 32 can simply be manufactured as a jagged surface or, generally, a non-smooth surface to facilitate more effective disruption of particles contained within it.

Figure 8:
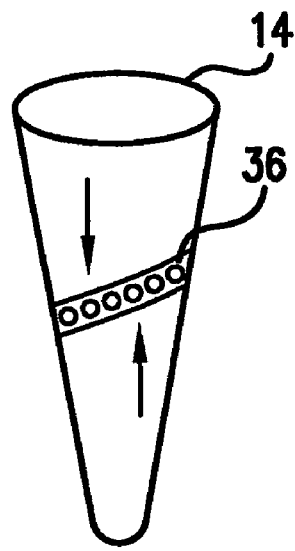
FIG. 8 is a schematic diagram of a vial having an internal grill in accordance with embodiments of the invention.

FIG. 8 is a schematic diagram of a vial 14 having an internal grill 32. Grill 32 can have openings of sufficient size and shape to facilitate more effective disruption. The openings can be sharpened or smooth according to need. In operation, samples within vial 14 cross grill 36 and become additionally disrupted. This, as is the case with irregular disrupting particles 16, leads to more effective processing.

Figure 9:
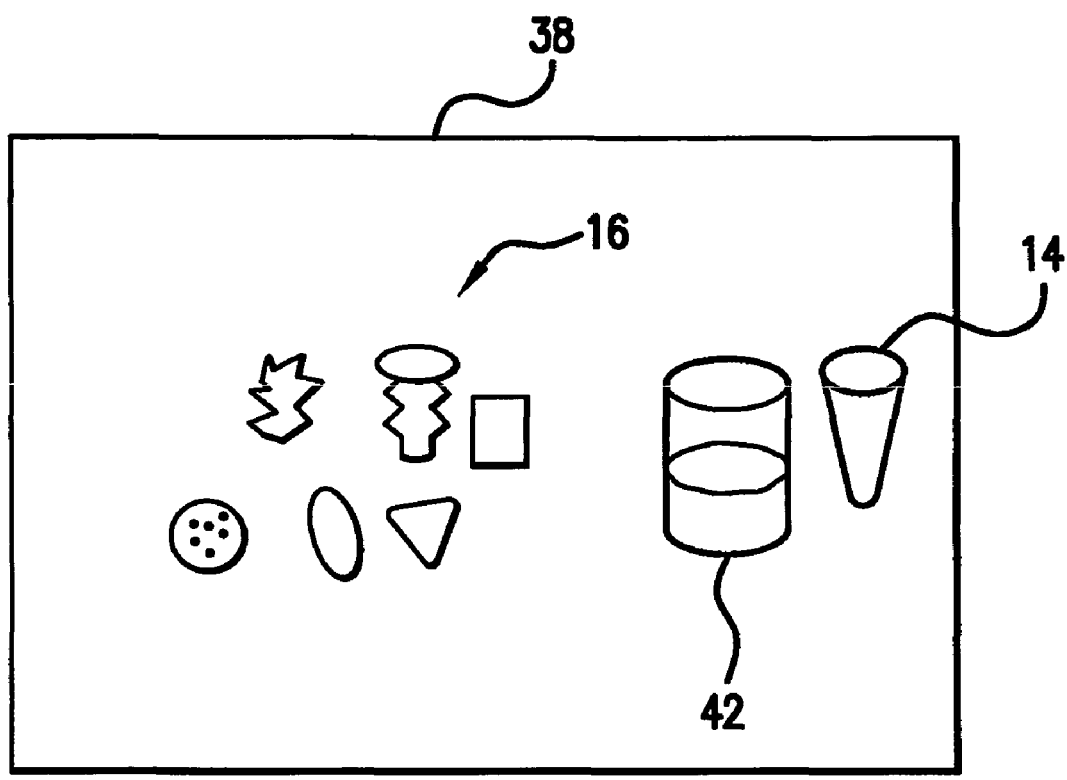
FIG. 9 is a schematic diagram of a kit in accordance with embodiments of the invention.

FIG. 9 is a schematic diagram of a kit 38. Kit 38 is a container suitable to hold disrupting particles 16, lysis buffer 42, and (optionally) vial 14. Of course, additional material can be added to this kit. Lysis buffer 42 can be any buffer known in the art. The particles 16 can be any of those described here, as is true with vial 14.

With the benefit of the present disclosure, those having skill in the art will comprehend that techniques claimed here and described above may be modified and applied to a number of additional, different applications, achieving the same or a similar result. The claims attached here cover all such modifications that fall within the scope and spirit of this disclosure.

The following examples are included to demonstrate specific embodiments of this disclosure. It should be appreciated by those of skill in the art that the techniques disclosed in the examples that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Using a MINIBEADBEATER, the inventors attempted to disrupt a relatively large tissue sample (400 mg) of mouse liver using 1 mM ceramic beads (Matrix D) which QBIO-GENE recommends for tissue lysis of large tissue samples. No disruption was detected even after 5 minutes of shaking on the highest setting. The inventors then implemented aspects of this disclosure in an attempt disruption in the MINIBEADBEATER using a more dense grinding material characterized by the following features: 1) an irregular and sharp surface; and 2) a heterogeneous population of small and large particles.

It was thought that a disruptive metal surface would be most effective when the shearing surface is roughly the same size as the target tissue particulate. As such, a combination of both larger and smaller particles may be needed to provide optimal shearing both at the start of the disruption (when the tissue is large and intact), as well as later stages in the disruption cycle (when the tissue particles are much smaller).

Figure 10:
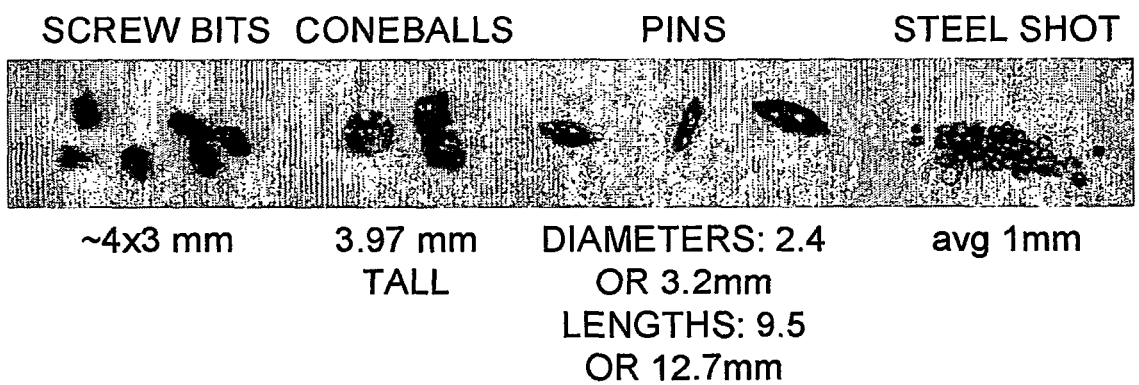
FIG. 10 is a photograph of representative disrupting particles in accordance with embodiments of the invention.

GLEN MILLS (Clifton N.J.) supplies a variety of shapes and sizes of commercial stainless steel bearings that can be used for disruption. The inventors achieved success with home-made "shrapnel" by cutting up a 2" wallboard screw (GRIP RITE) into ~4 mm bits using bolt cutters. Exemplary media is described below and shown in FIG. 10, which is a photograph of screw bits, coneballs, pins, and steel shot that can be used for disrupting particles 16.

The screw bits were soaked in RNase Zap for 1 hour and rinsed with copious amounts of Nuclease-free water. A 2 ml tube containing the shrapnel (~2 g), buffer (1.5 ml), and liver (400 mg) was shaken for 6×50 sec intervals on max speed setting in the MINIBEADBEATER. The sample was checked for disruption between each cycle. After approximately 3 minutes, the sample was completely disrupted. As a control, 400 mg of liver was ground up using a polytron for approximately 45 seconds. For both samples, RNA was prepared using RNaqueous and RNA quality was determined using an AGILENT RNA chip. (Table 1)

TABLE 1

Effectiveness of Irregular Beadbeating Matrices Compared to Polytron.

| Buffer, Grind apparatus | Tissue | treatment | Grind time | 28S/18S Quality | starting total(mg) |
|---|---|---|---|---|---|
| Lysis buffer, polytron | Mouse liver | Later-ice | 45 sec | 1.05 | 400 mg |
| Lysis buffer, screws | Mouse liver | Later-ice | 300 sec | 0.81 | 400 mg |
| Lysis buffer, polytron | Pig Node | RNAlater | 190 sec | 0.83 | 150 mg |
| Lysis buffer, coneballs | Pig Node | RNAlater | 190 sec | 1.16 | 150 mg |

Figure 11A:
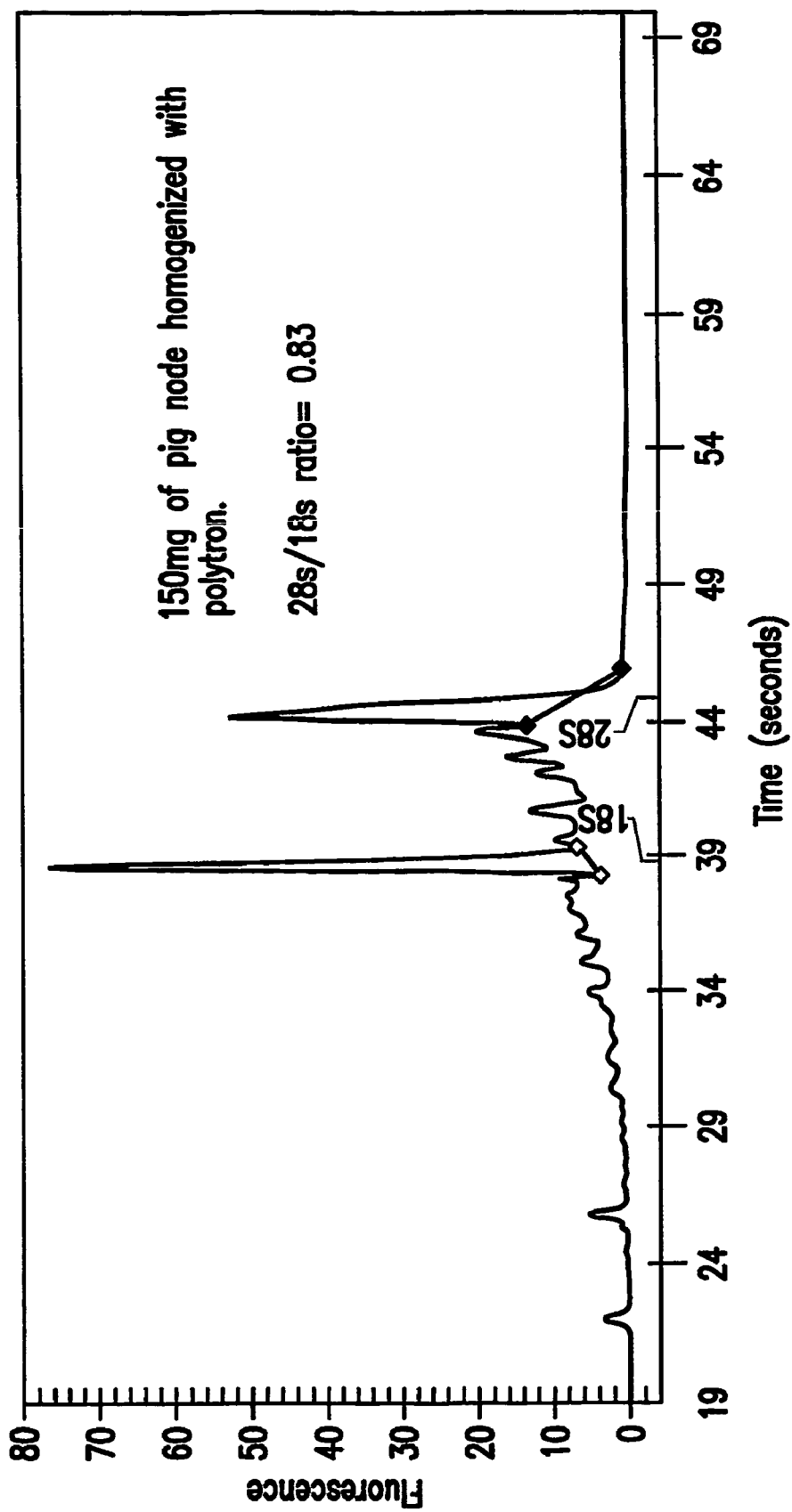
FIGS. 11A-B show two graphs demonstrating, among other things, increased yield of nucleic acids, in accordance with embodiments of the invention.
Figure 11B:
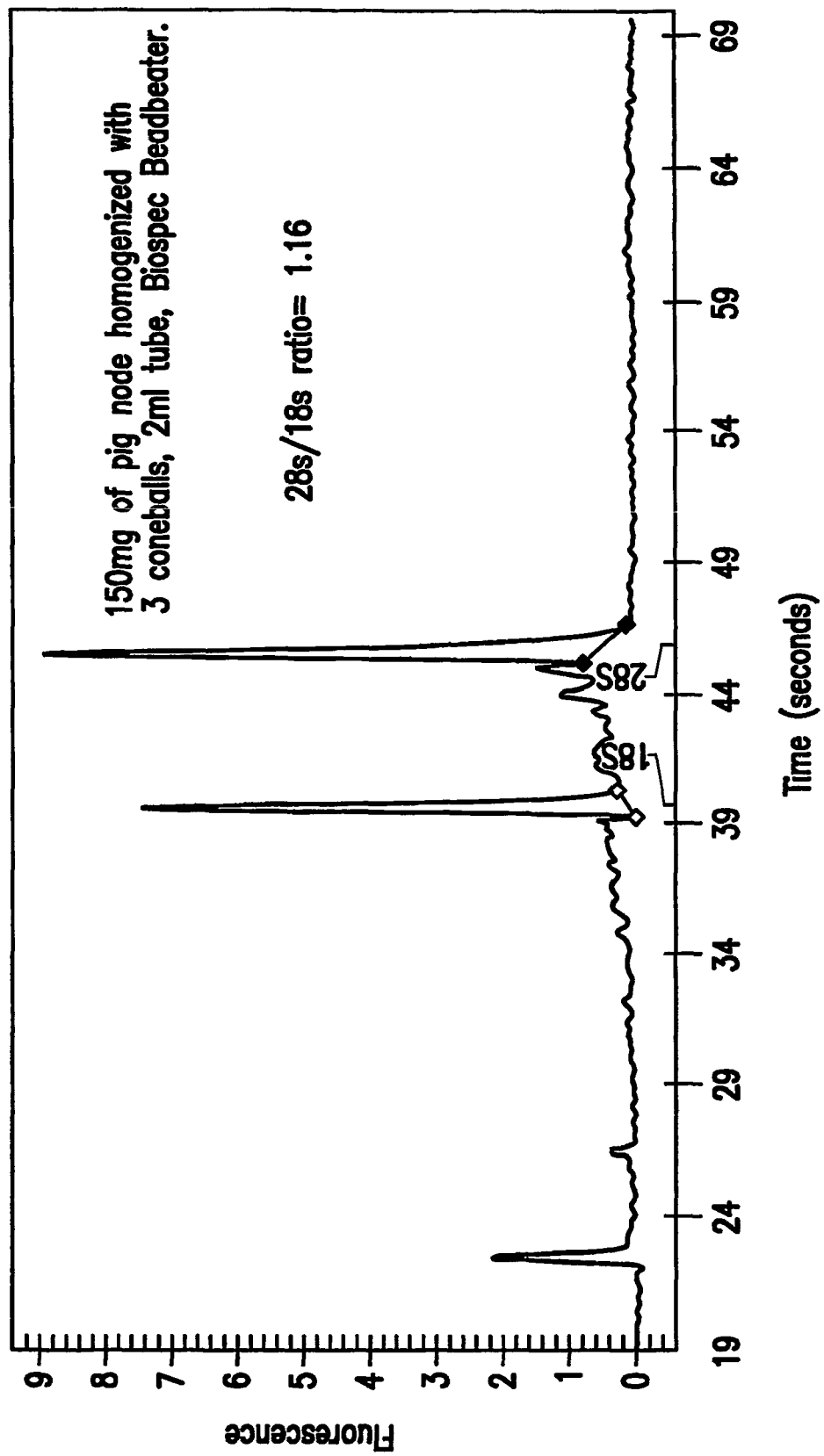
Figure 12:
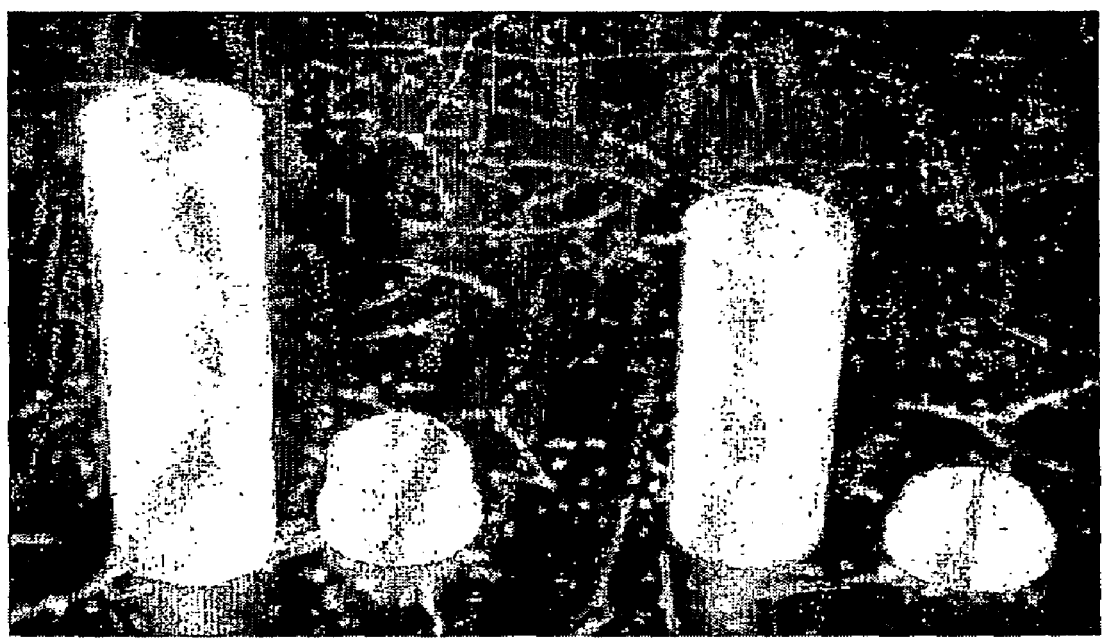
FIG. 12 is a photograph of modified vials in accordance with embodiments of the invention.

The results show that disruption with screws was similar to the polytron preparation both in yield and RNA quality. (see FIG. 11; note that this tissue was previously frozen).

Testing on GLEN MILLS samples showed that 3-5 coneballs worked well to disrupt 150 mg of pig lymph node tissue in 1300 μl of lysis buffer during a 190 second agitation. The inventors were able to purify RNA with 28/18S ratio of 1.16, which surpassed the quality of an equal-mass sample homogenized with the polytron. (Table 1). Other shapes did not work as well or, in one case, fractured the 2 ml tube during agitation (3.2×12.7 mm pins). The inventors believe that the combination of increased mass and a sharp and irregular surface of the grinding media can be used with good results and can be used in combination with less expensive shakers such as the MINIBEADBEATER With the techniques of this disclosure in mind, one can formulate recommended grinding media for different sample types to produce a kit that could interface with existing kits, such as RNaqueous kits.

The inventors also found that RNA quality can be improved by increasing the buffer to sample ratio. The inventors tested RNA quality as a function of increasing sample mass using the polytron and a fixed buffer volume. The table below shows the decrease in 28/18S ratio as the tissue mass increases from 50 to 500 mg (pig lymph node). The same was true in an experiment on mouse liver disrupted with screw parts. This indicates that RNA quality seems to drop as the lysis buffer gets "diluted" with the tissue sample as it dissociates. In fact, the effective guanidine concentration in the sample decreases as the tissue mass increases (3.9 M for a 50 mg sample to 3.25 M for a 300 mg sample; lysis buffer is 4M guanidine). As the guanidine concentration decreases below ~3.5M, RNases will invariably become active.

TABLE 2

RNA quality as a function of the ration of tissue mass to lysis buffer.

| Tissue | (mg) | % ground | (sec) | buffer | media | (g) | 28/18S |
|---|---|---|---|---|---|---|---|
| Pig Node | 50 | 100 | 190 | Lysis | polytron | n/a | 1.05 |
|  | 100 | 100 | 190 | Lysis | polytron | n/a | 0.99 |
|  | 150 | 100 | 190 | Lysis | polytron | n/a | 0.83 |
|  | 225 | 100 | 190 | Lysis | polytron | n/a | 0.8 |
|  | 300 | 100 | 190 | Lysis | polytron | n/a | 0 |
|  | 500 | 100 | 190 | Lysis | polytron | n/a | 0 |

TABLE 2-continued

RNA quality as a function of the ration of tissue mass to lysis buffer.

| Tissue | (mg) | % ground | (sec) | buffer | media | (g) | 28/18S |
|---|---|---|---|---|---|---|---|
| Mouse Liver | 110 | 100 | 160 | Lysis | Screws | 2 | 1.05 |
|  | 400 | NA | 300 | Lysis | Screws | 2 | 0.81 |
|  | 500 | 75 | 300 | Lysis | Screws | 2 | 0.61 |

QBIOGENES FASTPREP machine is regarded as one of the industry's leading devices in tissue homogenization. This instrument, like all other beadbeater-style machines, is recommended to be used with uniform, 1 mm spheres as the disruption media. After evaluation with swine lymph nodes and mouse liver with this matrix (QBIOGENE matrix D), the FASTPREP proved inferior to techniques of this disclosure. However, when the FASTPREP machine used coneballs in lieu of ceramic beads (even at the same weight), up to 250 mg tissues could be homogenized within 20-30 seconds. By making this modification, the inventors have improved the efficacy and efficiency of the homogenization process by 2.5- to 6-fold (Table 3).

Homogenizing tissue in a rapidly oscillating, irregular shaped matrix has proven beneficial. Table 3 compares disruption efficiencies with regard to grinding media and machine type. Samples of mouse liver (250 mg) stored in RNA-Later were disrupted in 1500 ul of lysis buffer using 2 coneballs or QBIOGENE Matrix D (1 mM ceramic beads) in the FASTPREP or the BEADBEATER. A standard curve was generated using a polytron to disrupt increasing masses of tissue in 1500 ul of lysis buffer. Percent disruption is presented two ways. Method A is a ratio of the residual tissue mass to the input amount. Method B compares disruption efficiencies on the basis of absorbance at 400 nM as generated by the standard curve (presumably due to heme absorbance). Since it is difficult to accurately weigh residual bits of tissue, the inventors believe comparison by OD may be a better predictor of percent disruption and should be an effective method to quantify disruption in future experiments. Interestingly, RNA quality for all of these samples is equivalent to the "gold standard" polytron samples.

TABLE 3

Irregularly-shaped, Jagged Beads Dramatically Accelerate Mouse Liver Tissue Disruption Compared to Conventional Beads in Two Commercial Beadbeater Instruments. Matrix D is composed of 1.4 mm ceramic beads and is recommended for use with both the FASTPREP and the BEADBEATER.

|  | Matrix | Machine | mg | Disruption Time (sec) | 28/18S | ng/ul | % Disruption (A) | OD400 | % Disruption (B) |
|---|---|---|---|---|---|---|---|---|---|
| 1 | 2 Coneballs | FastPrep | 250 mg | 30 sec | 1.08 | 650 | 96 | 0.92 | 92.00 |
| 2 | Matrix D | FastPrep | 250 mg | 30 sec | 1.08 | 254 | 59.52 | 0.58 | 70.00 |
| 3 | 2 Coneballs, 0.5 g Zirc | FastPrep | 250 mg | 30 sec | 1 | 319 | 88 | 0.88 | 90.00 |
| 4 | 5 coneballs | BeadBeater | 250 mg | 130 sec | 1.13 | 427 | 96 | 0.78 | 84.00 |
| 5 | 3 coneballs | BeadBeater | 250 mg | 130 sec | 1.18 | 296 | 49.2 | 0.51 | 66.00 |
| 6 | 3 coneballs, 1 g Zirc | BeadBeater | 250 mg | 130 sec | 0.99 | 194 | 16 | 0.27 | 43.00 |
| 7 | Matrix D | BeadBeater | 250 mg | 130 sec | 1.12 | 71.8 | 16 | 0.16 | 29.00 |
| 8 | Polytron Control | Polytron | 10 mg | 10 sec | 0.97 | 792 | 100 | 0.04 | 4.00 |
| 9 | Polytron Control | Polytron | 50 mg | 10 sec | 0.98 | 496 | 100 | 0.18 | 32.40 |
| 10 | Polytron Control | Polytron | 150 mg | 10 sec | 1.04 | 357 | 100 | 0.40 | 56.80 |
| 11 | Polytron Control | Polytron | 250 mg | 20 sec | 1.14 | 452 | 100 | 1.10 | 100.00 |

In some experiments, the inventors were limited by standard tube capacity—standard 2 ml tubes. To get around this, the inventors designed and tested a prototype tube made from a scintillation vial that was tried down to fit in the BEADBEATER clip (~36 mm). This allows for volumes of up to 5 ml to be added. A preliminary experiment showed that a 1.1 g sample of mouse liver could be completely disrupted in 2.7 ml of lysis buffer with 11 coneballs during a 150 second agitation in the bead beater. This sample was not analyzed for RNA quality, but the experiment shows larger sized tissue samples can be disrupted while maintaining RNA quality. The inventors were unable to find commercially-available tubes with these dimensions, and thus a custom tube may need to be manufactured.

Internal Grill

In other embodiments, one can use a vial or tube affixed with a metal (or other material) grill that spans a region (e.g., the midpoint diameter) of the tube. Shaking shears a sample as it crosses the grating. Data suggests that RNA of comparable quality and yield can be prepared using <200 mg of tissue and a lysis buffer such as is currently used in MELT, with 2% SDS to help curb RNase activity. Using this buffer system, it may be possible to combine MELT technology and closed-tube disruption for a more rapid, more efficient disruption step. Since enzymes such as proteinase K work well in 2% SDS and have been shown to drastically digest RNase in solution (data not shown), this combination can be promising for RNase protection during disruption. This approach can also "sanitize" the solution free of RNases such that the RNA is stable in the MELT buffer for an extended period to enable transport/storage.

To increase the appeal of this approach, it is desirable to interface with readily available laboratory equipment. AMBION currently sells a vortex attachment for its Microbe express kit. One can optimize disruption particle size and maximum amount of tissue that could be disrupted using the existing attachment. Since the vortex shakes within a smaller range of motion than the MINIBEADBEATER, tissue samples would have to be small (~10 mg). The MM 300 is designed for 30 mg, which could be matched using techniques of this example.

A preferred method would be to complete tissue disruption by simply vortexing the tube. In this fashion, one would only need to produce a specialized tube system for disruption or an attachment that would turn a vortex into the equivalent of a MIMIBEADBEATER To implement in-tube tissue disruption, one can use, for example: (1) a tube with a razor or other shearing surface fixed across its middle or another region, and/or (2) a tube with razor points or other relatively sharp protrusions on one or more of the walls. To implement such approaches, the force of the vortexing liquid on the sample must be high enough to allow the razor or other disruption aids to cut or adequately disrupt the sample.

EXAMPLE 2

The inventors have performed experiments that compare steel coneballs (asymmetric) with steel spheres (symmetric) and found that both were superior to the standard matrix (1.4 mm ceramic beads). The inventors found that the irregular-shaped matrices appear to be the best, by approximately 20%, as determined in a model system using liver tissue. This value and/or conclusion may be different for tougher tissues than liver, or different masses of tissue.

The specifications for the experiments are as follows:
Coneballs are 4×5×6 mm, 0.60 g/piece
$3/16$ spheres are 4.76 mm, 0.45 g
$7/32$ spheres are 5.56 mm, 0.69 g
Diagonals, 0.75 g (diagonals being cylindrical structures having angled ends)
Small Diagonals, 0.23 g
The data are as follows:

TABLE 4

Efficiency of Tissue Disruption as a Function of Bead Type, Size, and Number

| Media | (250 mg input) | | Relative Disruption Efficacy [(250-Tissue left(media))/ (250-Tissue left(std, 5 coneballs))] |
|---|---|---|---|
| | Tissue left | Total wt of beads | |
| 5 Coneballs | 0.123 (0.032) | 3.0 g | 1.00 |
| 5, $3/16$ spheres | 0.139 | 2.25 g | 0.87 |
| 5, $7/32$ spheres | 0.136 | 3.65 g | 0.90 |
| 6, $3/16$ spheres | 0.175 | 2.7 g | 0.59 |
| 5 Diagonals | 0.109 | 3.75 g | 1.11 |
| 5 small diagonals + 3 coneballs | 0.198 | 2.95 g | 0.41 |
| 3 coneballs + 3 $3/16$ spheres | 0.151 | 3.15 g | 0.78 |

Thus, the steel spheres appear to be superior to the current matrices. In particular, it appears that using larger spherical grinding media than is currently used would be advantageous. More particularly, if one were to use spherical media having a diameter, in one embodiment, larger than 4 mm, advantageous disruption efficiencies can be obtained. In other embodiments, the diameter may be 4.5 mm, 5 mm, 5.5 mm, 6 mm, 6.5 mm, 7 mm, 7.5 mm, 8 mm, 8.5 mm, 9 mm and so on (or values in between). Still in other embodiments, use of any grinding media larger than the standard 2.5 mm beads (or smaller) can offer improved results.

Use of larger media such as that used in the experiments of this example runs contra to conventional wisdom. Currently, 0.5 to 2.5 mm beads are recommended. Although manufacturers may list larger beads, those are referenced for plating bacteria, which is an unrelated application. For example, the webpage at http://www.biospec.com/Beads.htm represents conventional wisdom in this regard and recommends use of 0.1 mm glass beads when working with bacteria. When working with yeast/fungi, it recommends 0.5 mm diameter glass beads. When working with most tissue, it recommends using 1.0 mm diameter glass beads. When working with skin or plant material, it recommends 2.5 mm beads. When working with tough samples, it recommends using the same size beads (as above) but to use a more dense material. For example, most researchers prefer 0.1 mm zirconia-silica beads for disruption of spores or 2.5 mm zirconia beads or stainless steel beads for extraction of fibrous plant material. For plating of yeast and bacteria, the web page recommends adding a few 6.3 mm diameter glass beads to a plate to evenly spread yeast and bacteria. It instructs one to pack roller tubes or vials with 6.3 mm diameter glass beads to greatly increase surface area for tissue culture growth.

For reference, the web page lists typical densities of media. Glass Beads have a density of 2.5 g/cc. Zirconia/Silica Beads have a density of 3.7 g/cc. Zirconia Beads have a density of 5.5 g/cc. Stainless Steel Beads have a density of 7.9 g/cc. Tungsten Carbide Beads have a density of 14.9 g/cc. Beads commercially available from the web site are:
Cat. No. 11079101 Glass Beads, 0.1 mm Diameter
Cat. No. 11079105 Glass Beads, 0.5 mm Diameter
Cat. No. 11079110 Glass Beads, 1.0 mm Diameter
Cat. No. 11079125 Glass Beads, 2.5 mm Diameter
Cat. No. 11079135 Glass Beads, 3.5 mm Diameter
Cat. No. 11079635 Glass Beads, 6.35 mm
Cat No. 11079101z Zirconia/Silica Beads 0.1 mm
Cat. No. 11079105z Zirconia/Silica Beads 0.5 mm
Cat. No. 11079110z Zirconia/Silica Beads 1.0 mm
Cat. No. 11079125z Zirconia/Silica Beads 2.5 mm
Cat No. 11079107zx Zirconia Beads, 0.7 mm Cat. No. 11079110zx Zirconia Beads, 1.0 mm
Cat. No. 11079124zx Zirconia Beads, 2.4 mm
Cat. No. 11079112ss Stainless-Steel Beads, 1.2 mm
Cat. No. 11079123ss Stainless-Steel Beads, 2.3 mm
Cat. No. 11079132ss Stainless-Steel Beads, 3.2 mm
Cat. No. 11079635ss Stainless-Steel Beads, 6.35 mm
Cat. No. 11079132c Chrome-Steel Beads, 3.2 mm
Cat. No. 11079635c Chrome-Steel Beads, ¼ inch
Cat No. 11079111wc Tungsten-Carbide Beads, 1.1 mm With the benefit of the present disclosure, those having skill in the art will comprehend that techniques claimed here may be modified and applied to a number of additional, different applications, achieving the same or a similar result. For instance, sizes of different disrupting media may vary according to need. Particularly, screw-bits, cone balls, pins, non-spherical shot, diagonals, spheres or other media in accordance with embodiments here can have, e.g. but not limited to, a largest dimension equal to about 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, 5.1 mm, 5.2 mm, 5.3 mm, 5.4 mm, 5.5 mm, 5.6 mm, 5.7 mm, 5.8 mm, 5.9 mm, 6.0 mm, 6.1 mm, 6.2 mm, 6.3 mm, 6.4 mm, 6.5 mm, 6.6 mm, 6.7 mm, 6.8 mm, 6.9 mm, 7.0 mm, 7.1 mm, 7.2 mm, 7.3 mm, 7.4 mm, 7.5 mm, 7.6 mm, 7.7 mm, 7.8 mm, 7.9 mm, 8.0 mm, 8.1 mm, 8.2 mm, 8.3 mm, 8.4 mm, 8.5 mm, 8.6 mm, 8.7 mm, 8.8 mm, 8.9 mm, 9.0 mm, 9.1 mm, 9.2 mm, 9.3 mm, 9.4 mm, 9.5 mm, 9.6 mm, 9.7 mm, 9.8 mm, 9.9 mm, 10.0 mm, etc. (and values in between). Densities of media used can be, e.g. but not limited to, 0.5 g/cc, 1.0 g/cc, 1.5 g/cc, 2.0 g/cc, 2.5 g/cc, 3.0 g/cc, 3.5 g/cc, 4.0 g/cc, 4.5 g/cc, 5.0 g/cc, 5.5 g/cc, 6.0 g/cc, 6.5 g/cc, 7.0 g/cc, 7.5 g/cc, 8.0 g/cc, 8.5 g/cc, 9.0 g/cc, 9.5 g/cc, 10.0 g/cc, 10.5 g/cc, 11.0 g/cc, 11.5 g/cc, 12.0 g/cc, 12.5 g/cc, 13.0 g/cc, 13.5 g/cc, 14.0 g/cc, 14.5 g/cc, 15.0 g/cc, 15.5 g/cc, 16.0 g/cc, 16.5 g/cc, 17.0 g/cc, 17.5 g/cc, 18.0 g/cc, etc. (and values in between).

FIG. 13 illustrates different representative, but not limiting, media and dimensions that may be used with embodiments of the invention. Illustrated in FIG. 13 are pins, diagonals, and cone balls.

Other embodiments can utilize products that have been used previously for burnishing metals, as long as those products are of sufficient size and shape to effect suitable disruption. The inventors believe that shapes useful in burnishing can be useful in applications discussed here. For example, one can use shapes such as, but not limited to, eclipses (flat end ball) and/or beveled cylinders. One commercial provider of burnishing equipment that can find application here is TECH-NOCON ENGINEERS, India, which has a web page at http://www.steelmedia.com.

The attached claims hereto cover all such modifications that fall within the scope and spirit of this disclosure.

REFERENCES

Each of the following references is incorporated by reference in its entirety:
U.S. Pat. No. 6,258,930
U.S. Pat. No. 6,579,002

The invention claimed is:

1. An apparatus comprising a ball mill including disrupting particles that are not substantially spherical and comprise screw-bits, or non-spherical shot.

2. A method comprising disrupting a biological sample in a ball mill loaded with disrupting particles of claim 1.

3. The method of claim 2 wherein the disrupting particles comprise screw-bits.

4. The method of claim 2 wherein the disrupting particles comprise non-spherical shot.

5. The apparatus of claim 1 wherein the disrupting particles comprise screw-bits.

6. The apparatus of claim 1 wherein the disrupting particles comprise non-spherical shot.

* * * * *